US00PP13713P29

(12) United States Plant Patent
Hofmann

(10) Patent No.: US PP13,713 P2
(45) Date of Patent: Apr. 8, 2003

(54) NEW GUINEA IMPATIENS PLANT NAMED 'FISIMP 144'

(76) Inventor: Birgit Hofmann, Gassenweg 29, 56170, Bendorf (DE)

( * ) Notice: Subject to any disclaimer, the term of this patent is extended or adjusted under 35 U.S.C. 154(b) by 0 days.

(21) Appl. No.: 10/080,601

(22) Filed: Feb. 22, 2002

(51) Int. Cl.[7] ..... A01H 5/00
(52) U.S. Cl. ..... Plt./318

(58) Field of Search ..... Plt./318

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Fisimp 144', characterized by its outwardly spreading, rounded and uniformly mounded plant habit; freely branching and freely flowering habit; large dark purple-colored flowers that are positioned above and beyond the foliage; and medium green-colored leaves.

1 Drawing Sheet

BOTANICAL CLASSIFICATION/CULTIVAR DESIGNATION

*Impatiens hawkeri* cultivar Fisimp 144.

BACKGROUND OF THE INVENTION

The present Invention relates to a new and distinct cultivar of New Guinea Impatiens plant, botanically known as *Impatiens hawkeri,* and hereinafter referred to by the name 'Fisimp 144'.

The new Impatiens is a product of a planned breeding program conducted by the Inventor in Hillscheid, Germany. The objective of the breeding program is to develop new moderately compact Impatiens cultivars that flower relatively early with large rounded flowers and attractive flower colors.

The new Impatiens originated from a cross made by the Inventor in July, 1997 of the *Impatiens hawkeri* cultivar Swing, disclosed in U.S. Plant Pat. No. 9,338, as the female, or seed, parent with the *Impatiens hawkeri* cultivar Riviera Purple, not patented, as the male, or pollen, parent. The cultivar Fisimp 144 was discovered and selected by the Inventor as a flowering plant within the progeny of the stated cross in a controlled environment in Moncarapacho, Portugal in March, 1998.

Asexual reproduction of the new cultivar by terminal cuttings taken in Moncarapacho, Portugal, since March, 1998, has shown that the unique features of this new Impatiens are stable and reproduced true to type in successive generations.

SUMMARY OF THE INVENTION

The following traits have been repeatedly observed and are determined to be the unique characteristics of 'Fisimp 144'. These characteristics in combination distinguish 'Fisimp 144' as a new and distinct Impatiens cultivar:

1. Outwardly spreading, rounded and uniformly mounded plant habit.

2. Freely branching and freely flowering habit.

3. Large dark purple-colored flowers that are positioned above and beyond the foliage.

4. Medium green-colored leaves.

Plants of the new Impatiens can be compared to plants of the female parent, the cultivar Swing. In side-by-side comparisons conducted by the Inventor in Hillscheid, Germany, plants of the new Impatiens differed from plants of the cultivar Swing in the following characteristics:

1. Leaves of plants of the new Impatiens were green in color whereas leaves of plants of the cultivar Swing were reddish green in color.

2. Plants of the new Impatiens had darker purple-colored flowers than plants of the cultivar Swing.

Plants of the new Impatiens can be compared to plants of the male parent, the cultivar Riviera Purple. In side-by-side comparisons conducted by the Inventor in Hillscheid, Germany, plants of the new Impatiens differed from plants of the cultivar Riviera Purple in the following characteristics:

1. Plants of the new Impatiens were not as compact as plants of the cultivar Riviera Purple.

2. Plants of the new Impatiens had larger and darker green-colored leaves than plants of the cultivar Riviera Purple.

3. Flowers of plants of the new Impatiens were not as red purple in color as flowers of plants of the cultivar Riviera Purple.

Plants of the new Impatiens can also be compared to plants of the cultivar Kipas, disclosed in U.S. Plant Pat. No. 10,432. In side-by-side comparisons conducted by the Inventor in Hillscheid, Germany, plants of the new Impatiens differed from plants of the cultivar Kipas in the following characteristics:

1. Plants of the new Impatiens were taller and more broad than plants of the cultivar Kipas.

2. Plants of the new Impatiens had shorter internodes than plants of the cultivar Kipas.

3. Plants of the new Impatiens had larger leaves than plants of the cultivar Kipas.

4. Flowers of plants of the new Impatiens were darker purple in color than flowers of plants of the cultivar Kipas.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new Impatiens. The photograph comprises a side perspective view of a typical flowering plant of 'Fisimp 144' grown in a container.

DETAILED BOTANICAL DESCRIPTION

The cultivar Fisimp 144 has not been observed under all possible environmental conditions. The phenotype may vary somewhat with variations in environment such as temperature and light intensity, without, however, any variance in genotype.

The aforementioned photographs, following observations and measurements describe plants grown in Langley, British Columbia, Canada, under commercial practice in a greenhouse. Rooted young plants were planted in 17.5-cm containers during the spring and the aforementioned photograph and following observations and measurements were taken during the summer about 17 weeks later. During the production of the plants, day temperatures ranged from 21 to 24° C. and night temperatures were about 17 to 18° C. In the following description, color references are made to The Royal Horticultural Society Colour Chart, 1995 Edition, except where general terms of ordinary dictionary significance are used.

Botanical classification: *Impatiens hawkeri* cultivar Fisimp 144.

Parentage:

*Female parent.*—*Impatiens hawkeri* cultivar Swing, disclosed in U.S. Plant Pat. No. 9,338.

*Male parent.*—*Impatiens hawkeri* cultivar Riviera Purple, not patented.

Propagation:

*Type cutting.*—Terminal tip cuttings.

*Time to initiate roots.*—Summer: About 8 to 9 days at 24° C. Winter: About 10 days at 21° C.

*Time to produce a rooted cutting.*—Summer: About 15 days at 24° C. Winter: About 18 days at 21° C.

*Root description.*—Numerous, fibrous, and freely branching; 179D in color.

Plant description:

*General appearance.*—Outwardly spreading, low, rounded and uniformly mounded plant growth habit; freely branching habit, dense and bushy appearance; freely flowering. Moderately vigorous.

*Crop time.*—From a rooted cutting, about 10 to 11 weeks are required to produce finished flowering plants in 12-cm containers.

*Plant height.*—About 20.5 cm.

*Plant diameter or spread.*—About 55.1 cm.

*Lateral branches.*—Quantity per plant: About 9. Length: About 19 cm. Diameter: About 8 mm. Internode length: About 3 cm. Color: 181A to 185A.

*Foliage description.*—Arrangement: Primarily in whorls. Length: About 16.7 cm. Width: About 5 cm. Shape: Elliptic. Apex: Acuminate. Base: Acute. Margin: Serrulate with ciliation. Texture: Smooth, slightly rugose; glabrous. Color: Young foliage, upper surface: 137C. Young foliage, lower surface: 139C. Fully expanded foliage, upper surface: 137A. Fully expanded foliage, lower surface: 139C. Venation, upper surface: 137A; towards the base, 47A. Venation, lower surface: 53C. Petiole: Length: About 2.75 cm. Diameter: About 3.5 mm. Color: Upper surface: 47A to 53D. Lower surface: 53B to 53C.

Flower description:

*Flower type and flowering habit.*—Single; large dark purple-colored flowers. Freely and continuously flowering; usually about 6 to 9 flowers and flower buds per lateral branch. Flowers flat and positioned above and beyond the foliage and typically face parallel to the leaf canopy. Petals not persistent; gynoecium persistent. Flowers not fragrant.

*Flower longevity.*—Flowers last about 8 to 9 days on the plant.

*Flowering season.*—Year-round under greenhouse conditions. Plants begin flowering about 10 to 11 weeks after planting.

*Flower buds.*—Length: About 1.9 cm. Diameter: About 1.5 cm. Shape: Ovoid. Color: 74A to 78A.

*Flower length.*—About 7.3 cm.

*Flower width.*—About 7.2 cm.

*Flower depth.*—About 2 cm.

*Petals.*—Quantity: Five per flower, imbricate. Length: Banner petals: About 3.2 cm. Lateral and base petals: About 3.6 cm. Width: Banner petal: About 5.3 cm. Lateral and base petals: About 4.2 cm. Shape: Roughly cordate. Apex: Emarginate; distinctly lobed. Base: Attenuate. Margin: Entire. Aspect: Slightly upright. Texture: Smooth; satiny. Color: When opening and fully opened, upper surface: 78A. When opening and fully opened, lower surface: 78B to 78C; towards base or eye, 74A, small; color fading towards 78C with subsequent development.

*Spur.*—Quantity: One per flower. Length: About 5.8 cm. Diameter: At apex: About 0.5 mm. At flower: About 3 mm. Aspect: Curved. Color: 53A to 53B.

*Peduncles.*—Length: About 5.3 cm. Diameter: About 2 mm. Strength: Strong, flexible. Angle: About 45° from the lateral branch. Color: 185B.

*Reproductive organs.*—Androecium: Stamen number: Five fused at anthers, hooded; filaments free. Anther length: About 6 mm. Anther shape: Obovate. Anther color: 74B. Pollen amount: Moderate. Pollen color: 8D. Gynoecium: Pistil quantity: One per flower. Pistil length: About 5 mm. Stigma color: 18D. Style color: 18D. Ovary: Five-celled. Ovary color: 143A.

*Seed/fruit.*—Seed and fruit development has not been observed.

Disease/pest resistance: Plants of the new Impatiens have not been observed to be resistant to pathogens and pests common to Impatiens.

It is claimed:

1. A new and distinct cultivar of New Guinea Impatiens plant named 'Fisimp 144', as illustrated and described.

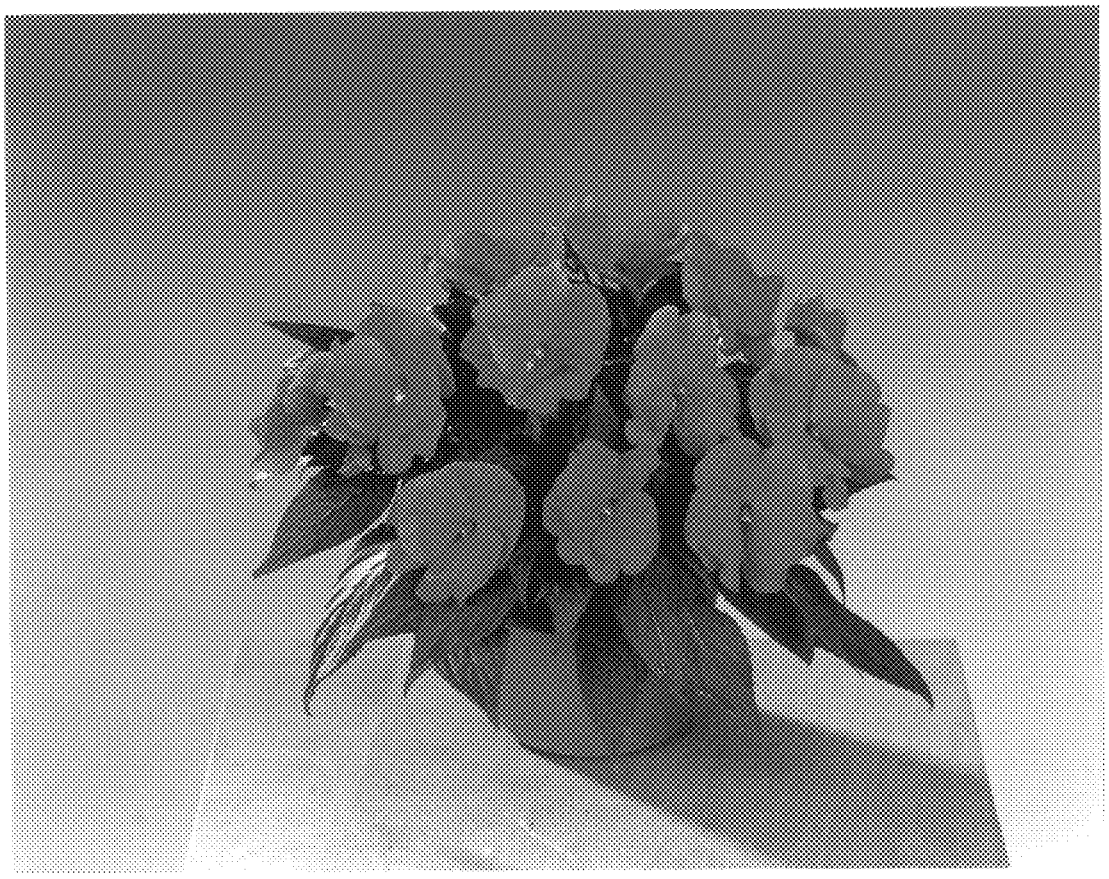

* * * * *